United States Patent
Funk et al.

(10) Patent No.: US 8,080,620 B2
(45) Date of Patent: Dec. 20, 2011

(54) PROCESS FOR CONTINUOUSLY PRODUCING WATER-ABSORBING POLYMER PARTICLES

(75) Inventors: Rüdiger Funk, Niedernhausen (DE); Matthias Weismantel, Jossgrund-Oberndorf (DE); Leigh R. Blair, Greenwood Springs, MS (US); Kevin D. Heitzhaus, Suffolk, VA (US)

(73) Assignee: BASF SE, Ludwigshafen (DE)

( * ) Notice: Subject to any disclaimer, the term of this patent is extended or adjusted under 35 U.S.C. 154(b) by 386 days.

(21) Appl. No.: 12/486,483

(22) Filed: Jun. 17, 2009

(65) Prior Publication Data

US 2009/0318633 A1 Dec. 24, 2009

Related U.S. Application Data

(60) Provisional application No. 61/073,914, filed on Jun. 19, 2008.

(51) Int. Cl.
*C08G 18/62* (2006.01)
*C08F 20/06* (2006.01)

(52) U.S. Cl. .................................. 525/451; 526/317.1

(58) Field of Classification Search .................. 525/451; 526/317.1
See application file for complete search history.

(56) References Cited

U.S. PATENT DOCUMENTS 5,064,582 A * 11/1991 Sutton et al. ............... 264/37.29

FOREIGN PATENT DOCUMENTS

| CA | 2195373 A1 | 7/1997 |
|---|---|---|
| EP | 0 463 388 A1 | 1/1992 |
| EP | 0 496 594 A2 | 7/1992 |
| EP | 0 785 224 A2 | 7/1997 |
| EP | 1 878 761 A1 | 1/2008 |
| EP | 1878761 A1 * | 1/2008 |

OTHER PUBLICATIONS

Buchholz et al., Modern Superabsorbent Polymer Technology, pp. 71-103 (1998).

* cited by examiner

*Primary Examiner* — Michael M Bernshteyn
(74) *Attorney, Agent, or Firm* — Marshall, Gerstein & Borun LLP

(57) ABSTRACT

A process for continuously producing water-absorbing polymer particles, comprising polymerization, drying, grinding, classification and at least partial recycling of the undersize obtained in the classification, wherein the polymer gel obtained by the polymerization is withdrawn from the polymerization reactor and mixed with the recycled undersize.

9 Claims, No Drawings

PROCESS FOR CONTINUOUSLY PRODUCING WATER-ABSORBING POLYMER PARTICLES

CROSS-REFERENCE TO RELATED APPLICATIONS

This application claims the benefit of U.S. provisional patent application No. 61/073,914, filed Jun. 19, 2008, incorporated by reference herein in its entirety.

The present invention relates to a process for continuously producing water-absorbing polymer particles, comprising polymerization, drying, grinding, classification and at least partial recycling of the undersize obtained in the classification, wherein the polymer gel obtained by the polymerization is withdrawn from the polymerization reactor and mixed with the recycled undersize.

The production of water-absorbing polymer particles is described, for example, in the monograph "Modem Superabsorbent Polymer Technology", F. L. Buchholz and A. T. Graham, Wiley-VCH, 1998, pages 71 to 103.

Water-absorbing polymers are used to produce diapers, tampons, sanitary napkins and other hygiene articles, but also as water-retaining agents in market gardening.

The properties of the water-absorbing polymers can be adjusted via the degree of crosslinking. With increasing degree of crosslinking, the gel strength increases and the centrifuge retention capacity (CRC) falls.

To improve the performance properties, for example permeability of the swollen gel bed (SFC) in the diaper and absorption under a pressure of 49.2 g/cm$^2$, water-absorbing polymer particles are generally surface postcrosslinked. This increases the degree of crosslinking of the particle surface, which allows the absorption under a pressure of 49.2 g/cm$^2$ and the centrifuge retention capacity (CRC) to be at least partially decoupled. This surface postcrosslinking can be carried out in the aqueous gel phase. However, preference is given to surface coating dried, ground and screened-off polymer particles (base polymer) with a surface postcrosslinker, thermally surface postcrosslinking them and drying them. Crosslinkers suitable for this purpose are compounds which comprise at least two groups which can form covalent bonds with the carboxylate groups of the water-absorbing polymers.

The water-absorbing polymers are used as a pulverulent, particulate product, preferably in the hygiene sector. Here, for example, particle sizes between 150 and 850 μm are used, and the particulate polymer material is classified to these particle sizes as early as in the production process. This is done by using continuous screening machines with at least two screens, using screens with mesh sizes of 150 and 850 μm. Particles with a particle size of up to 150 μm fall through both screens and are collected as undersize at the bottom of the screening machine. Particles with a particle size of greater than 850 μm remain as oversize on the uppermost screen and are discharged, ground again and recycled. The product fraction with a particle size of from greater than 150 to 850 μm is removed as midsize between the two screens of the screening machine.

The undersize and oversize obtained in the classification is typically recycled into the production process. The recycling of the undersize is described, for example, in EP 0 463 388 A1, EP 0 496 594 A2, EP 0 785 224 A2, EP 1 878 761 A1 and U.S. Pat. No. 5,064,582.

EP 0 463 388 A1 states that addition of a small amount of undersize can result in pumpable polymer gels with a high solids content.

EP 0 496 594 A2 teaches the recycling of the undersize into the polymerization reactor.

EP 0 785 224 A2 describes the recycling of the undersize into the polymer gel formed in the polymerization, with addition of surfactants.

EP 1 878 761 A1 discloses a process for recycling undersize coated with water-soluble polyvalent metal salts. The undersize can be mixed into the polymer gel, for example by means of a kneader.

U.S. Pat. No. 5,064,582 discloses a process for recycling undersize, wherein the undersize is mixed with water before the recycling.

It was an object of the present invention to provide an improved process for recycling the undersize obtained in the production of water-absorbing polymer particles.

The object was achieved by a process for continuously producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers specified under a) and
e) optionally one or more water-soluble polymers, comprising polymerization, drying, grinding, classification and at least partial recycling of the undersize obtained in the classification, the polymer gel obtained by the polymerization being withdrawn from the polymerization reactor and mixed with the recycled undersize in an extruder, wherein the water content of the mixture obtained by mixing the polymer gel withdrawn from the polymerization reactor with the recycled undersize is at most 70% by weight, essentially no surfactant is added in the mixing of the polymer gel withdrawn from the polymerization reactor with the recycled undersize and/or the surface tension of the aqueous extract of the water-absorbing polymer particles is at least 0.06 N/m.

It is important that the mixing is carried out in an extruder. In an extruder, a viscous mass can be pressed under high pressure through at least one shaping orifice. A very high mixing energy can be introduced in an extruder.

In the context of this invention, undersize refers to a particle size fraction which is obtained in the classification and has a smaller mean particle size than the particle size fraction of the target product. To remove the undersize, a screen with a mesh size of up to 300 μm is typically used. The mesh size of the screen is preferably at least 100 μm, more preferably at least 150 μm, most preferably at least 200 μm.

The water content of the polymer gel withdrawn from the polymerization reactor is preferably from 40 to 75% by weight, more preferably from 50 to 70% by weight, most preferably from 55 to 65% by weight.

The water content of the recycled undersize is preferably less than 8% by weight, more preferably less than 6% by weight, most preferably less than 5% by weight.

The low water content of the recycled undersize has the consequence that the undersize is metered into the mixing unit as a free-flowing powder.

The surface tension of the aqueous extract of the water-absorbing polymer particles is preferably at least 0.063 N/m, more preferably at least 0.066 N/m, most preferably at least 0.068 N/m.

Surfactant compounds lower the surface tension of the aqueous extract and hence increase the leakage rate of the diapers.

The water content of the mixture obtained by mixing the polymer gel withdrawn from the polymerization reactor with the recycled undersize is preferably from 40 to 68% by weight, more preferably from 50 to 65% by weight, most preferably from 55 to 62% by weight.

The polymer gel withdrawn from the polymerization reactor is preferably mixed with the recycled undersize for from 1 to 180 minutes, more preferably for from 2 to 60 minutes, most preferably for from 5 to 20 minutes.

During the mixing, water can be added additionally, if appropriate possibly in the form of an aqueous solution. However, it should be noted that too much water has an adverse effect on the mixing result.

The polymer gel withdrawn from the polymerization reactor is mixed with the recycled undersize at a temperature of preferably from 40 to 80° C., more preferably of from 45 to 75° C., most preferably of from 50 to 70° C.

The ratio of polymer gel to recycled undersize is preferably from 5 to 50, more preferably from 10 to 40, very particularly from 12 to 30.

The polymerization reactors usable for the process according to the invention are not subject to any restrictions.

In a static polymerization, it is not possible to mix in the undersize to be recycled during the polymerization. When the undersize, however, is added before the polymerization, this increases the degree of crosslinking of the resulting polymer, as a result of which the centrifuge retention capacity (CRC) falls. The process according to the invention is therefore particularly advantageous in a static polymerization, for example in the case of polymerization on a continuous belt.

The process according to the invention preferably comprises at least one surface postcrosslinking. In a particularly preferred embodiment of the present invention, the surface postcrosslinking is both preceded and followed by classification.

The present invention is based on the finding that the addition of undersize from the running process leads to a significant decline in the centrifuge retention capacity. This undesired effect can substantially be suppressed when the undersize is not added until just beyond the polymerization reactor.

The present invention is also based on the finding that the mixing result can be improved significantly when the water content in the course of mixing in the extruder is kept low. Only in this way is it possible to introduce a sufficiently great mixing energy and to break up undersize agglomerates which occur as intermediates. The previous pasting of the undersize with water, known from the prior art, or the addition of surfactants is no longer required.

The water-absorbing polymer particles are prepared by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions containing excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/38402 A1. Polymerization on a belt is described, for example, in DE 38 25 366 A1 and U.S. Pat. No. 6,241,928. Polymerization in a belt reactor forms a polymer gel, which has to be comminuted in a further process step, for example in a meat grinder, extruder or kneader.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 50 to 80 mol %, most preferably from 60 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably from 0.5 to 15% by weight, more preferably from 1 to 10% by weight, most preferably from 2 to 8% by weight, the residual moisture content being determined by the EDANA (European Disposables and Nonwovens Association) recommended test method No. WSP 230.2-05 "Moisture content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained (undersize). The solids content of the gel before the drying is preferably from 25 to 90% by weight, more preferably from 35 to 70% by weight, most preferably from 40 to 60% by weight. Optionally, it is, however, also possible to use a fluidized bed drier or a heated plowshare mixer for the drying operation.

Thereafter, the dried polymer gel is ground and classified, and the apparatus used for grinding may typically be single-or multistage roll mills, preferably two-or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of the EDANA (European Disposables and Nonwovens Association) recommended test method No. WSP 220.2-05 "Particle size distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles (undersize) should therefore be small.

Excessively small polymer particles are therefore typically removed and recycled into the process.

The proportion of particles having a particle size of at most 850 μm is preferably at least 90% by weight, more preferably at least 95% by weight, most preferably at least 98% by weight.

Polymer particles with too great a particle size lower the swell rate. The proportion of excessively large polymer particles (oversize) should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 83 022 A2, EP 543 303 A1 and EP 937 736 A2, di- or polyfunctional alcohols, as described in DE 33 14 019 A1, DE 35 23 617 A1 and EP 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1199 327 A2 and morpholine-2,3-dione and its derivatives in WO 2003/31482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably from 0.001 to 2% by weight, more preferably from 0.02 to 1% by weight, most preferably from 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with the surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers, plowshare mixers and paddle mixers. Particular preference is given to horizontal mixers such as plowshare mixers and paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, Lödige mixers, Bepex mixers, Nauta mixers, Processall mixers and Schugi mixers. However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio is preferably from 20:80 to 40:60.

The thermal drying is preferably carried out in contact driers, more preferably paddle driers, most preferably disk driers. Suitable driers are, for example, Bepex driers and Nara driers. Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably from 120 to 220° C., more preferably from 130 to 210°C., most preferably from 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened. Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably from 0 to 15% by weight, more preferably from 0.2 to 10% by weight, most preferably from 0.5 to 8% by weight, the water content being determined by the EDANA (European Disposables and Nonwovens Association) recommended test method No. WSP 230.2-05 "Moisture content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA (European Disposables and Nonwovens Association) recommended test method No. WSP 241.2-05 "Centrifuge retention capacity".

The water-absorbing polymer particles produced by the process according to the invention have an absorption under a pressure of 49.2 g/cm² of typically at least 15 g/g, preferably at least 20 g/g, preferentially at least 22 g/g, more preferably at least 24 g/g, most preferably at least 26 g/g. The absorption under a pressure of 49.2 g/cm² of the water-absorbing polymer particles is typically less than 35 g/g. The absorption under a pressure of 49.2 g/cm² is determined analogously to the EDANA (European Disposables and Nonwovens Association) recommended test method No. WSP 242.2-05 "Absorption under pressure", except that a pressure of 49.2 g/cm² is established instead of a pressure of 21.0 g/cm².

The water-absorbing polymer particles are tested by the test methods described below.
Methods:
The analyses should, unless stated otherwise, be performed at an ambient temperature of 23±2° C. and a relative air humidity of 50±10%. The water-absorbing polymer particles are mixed thoroughly before the analysis.
Residual Monomers
The residual monomers (Remos) are determined by the EDANA (European Disposables and Nonwovens Association) recommended test method No. WSP 210.2-05 "Residual Monomers".
Centrifuge Retention Capacity
The centrifuge retention capacity (CRC) is determined by the EDANA (European Disposables and Nonwovens Association) recommended test method No. WSP 241.2-05 "Centrifuge Retention Capacity".
Absorption Under a Pressure of 21.0g/cm²
The absorption under a pressure of 21.0 g/cm² is determined by the EDANA (European Disposables and Nonwovens Association) recommended test method No. WSP 242.2-05 "Absorption under Pressure".
Extractables
The extractables (Extr.) are determined by the EDANA (European Disposables and Nonwovens Association) recommended test method No. WSP 270.2-05 "Extractables".
Surface Tension of the Aqueous Extract (OFS)
0.20 g of the water-absorbing polymer particles is weighed into a small beaker (external diameter approx. 42 mm and height approx. 50 mm) and admixed with 40 ml of a 0.9% by weight salt solution. The contents of the beaker are stirred at 400 rpm with a magnetic stirrer bar (2.4 cm×0.5 cm) for 60 minutes, then left to stand for 2 minutes. Finally, the surface tension (OFS) of the supernatant aqueous phase is measured with a K10-ST digital tensiometer (Krüss GmbH; Hamburg; Germany) or comparable instrument with a platinum plate.

The EDANA test methods are, for example, obtainable from the European Disposables and Nonwovens Association, Avenue Eugène Plasky 157, B-1030 Brussels, Belgium.

EXAMPLES

Example 1

Preparation of Base Polymer A and Undersize A 1028 g of a 37.3% by weight aqueous sodium acrylate solution, 98 g of acrylic acid, 254 g of water and 1.29 g of 3-tuply ethoxylated glyceryl triacrylate were weighed into a 2000 ml metal cup. The degree of neutralization was 75 mol %. The metal cup was sealed with Parafilm® and inertized with 150 l/h of nitrogen. During the inertization, the monomer solution was cooled to −0.5° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish with a diameter of 190 mm. The glass dish was covered with a polymer film and likewise inertized with 150 l/h of nitrogen. In addition, the monomer solution was stirred in the glass dish by means of a magnetic stirrer bar. Subsequently, by means of a disposable syringe, 5.88 g of a 1% by weight aqueous solution of Brüggolite®FF6 (disodium salt of 2-hydroxy-2-sulfinatoacetic acid) were metered into the monomer solution. After the start of the reaction, the magnetic stirrer was switched off.

After a reaction time of 30 minutes, the polymer gel was removed and comminuted with an extruder with a perforated plate (hole diameter 6 mm), sprayed with 17.6 g of a 1% aqueous solution of sodium bisulfite and extruded twice.

The gel was distributed onto four metal sheets and dried at 160° C. in a forced-air drying cabinet for 1 hour. The loading of the metal sheets with polymer gel was 0.59 g/cm². This was followed by precomminution with a roll mill having a gap width of 1000 µm and homogenization with a rolling mixer.

A portion of approx. 100 g was comminuted with a two-stage roll mill with a gap width of 600 µm and 400 µm, and screened off to from 150 to 850 µm (base polymer A). The remaining amount was comminuted to a particle size of less than 150 µm by means of a rotor mill (Retsch® ZM200) (undersize A).

Example 2

Preparation of Base Polymer B and Undersize B

The procedure was as in Example 1. The amount of 3-tuply ethoxylated glyceryl triacrylate was lowered to 0.58 g.

Example 3

1028 g of a 37.3% by weight aqueous sodium acrylate solution, 98 g of acrylic acid, 254 g of water and 1.29 g of 3-tuply ethoxylated glyceryl triacrylate were weighed into a 2000 ml metal cup. The degree of neutralization was 75 mol %. The metal cup was sealed with Parafilm® and inertized with 150 l/h of nitrogen. During the inertization, the monomer solution was cooled to −0.5° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish with a diameter of 190 mm. The glass dish was covered with a polymer film and likewise inertized with 150 l/h of nitrogen. In addition, the monomer solution was stirred in the glass dish by means of a magnetic stirrer bar. Subsequently, by means of a disposable syringe, 5.88 g of a 1% by weight aqueous solution of Brüggolite®FF6 (disodium salt of 2-hydroxy-2-sulfinatoacetic acid) were metered into the monomer solution. After the start of the reaction, the magnetic stirrer was switched off.

After a reaction time of 30 minutes, the polymer gel was removed and comminuted with an extruder with a perforated plate (hole diameter 6 mm), sprayed with 17.6 g of a 1% aqueous solution of sodium bisulfite and extruded twice. Subsequently, a total of 84 g of undersize A from Example 1 in two portions was powdered by means of a 180 μm screen and a spoon, and extruded for a third time.

The gel was distributed onto four metal sheets and dried at 160° C. in a forced-air drying cabinet for one hour. The loading of the metal sheets with polymer gel was 0.59 g/cm². This was followed by precomminution with a roll mill having a gap width of 1000 μm and comminution with a second roll mill with a gap width of 600 μm and 400 μm, and screening off to from 150 to 850 μm.

The resulting polymer particles were analyzed. The results are compiled in the table.

Example 4 to 7

The procedure was as in Example 3. Together with the metered addition of the undersize, 0.0166 or 0.0819% by weight of sorbitan monococoate or sorbitan monolaurate, in each case in 1% by weight of water, based in each case on the polymer gel, was sprayed onto the polymer gel.

The resulting polymer particles were analyzed. The results are compiled in the table.

Example 8

The procedure was as in Example 3. The amount of 3-tuply ethoxylated glyceryl triacrylate was lowered to 0.58 g and undersize B was used.

The resulting polymer particles were analyzed. The results are compiled in the table.

Examples 9 and 10

The procedure was as in Example 8. Together with the metered addition of the undersize, 0.0100 or 0.0166% by weight of sorbitan monococoate in 1% by weight of water, based in each case on the polymer gel, was sprayed onto the polymer gel.

The resulting polymer particles were analyzed. The results are compiled in the table.

The results show that the undersize can be recycled even without addition of surfactant in the extruder. The higher energy input leads only to an insignificant change in the extractables. Surprisingly, the process according to the invention also leads to a product with a significantly lowered content of residual monomers compared to the prior art.

TABLE

| Example | Surfactant | Amount | CRC | AUL | Extr. | OFS | Remos | <150 μm |
|---|---|---|---|---|---|---|---|---|
| Base polymer A | | | 31.4 g/g | 11.1 g/g | 13.2% by wt. | 72.7 mN/m | 0.30% by wt. | 4.7% by wt. |
| 3 | | | 31.1 g/g | 9.8 g/g | 14.9% by wt. | 71.0 mN/m | 0.17% by wt. | 8.3% by wt. |
| 4* | Sorbitan monococoate | 166 ppm | 29.8 g/g | 10.8 g/g | 13.0% by wt. | 59.3 mN/m | 0.50% by wt. | 7.0% by wt. |
| 5* | Sorbitan monococoate | 819 ppm | 30.5 g/g | 10.1 g/g | 13.4% by wt. | 51.2 mN/m | 0.39% by wt. | 6.4% by wt. |
| 6* | Sorbitan monolaurate | 166 ppm | 30.9 g/g | 10.3 g/g | 14.1% by wt. | 60.4 mN/m | 0.43% by wt. | 7.2% by wt. |
| 7* | Sorbitan monolaurate | 819 ppm | 30.6 g/g | 9.7 g/g | 13.5% by wt. | 57.7 mN/m | 0.48% by wt. | 6.7% by wt. |
| Base polymer B | | | 39.4 g/g | 7.9 g/g | 21.8% by wt. | 72.7 mN/m | 0.10% by wt. | 4.0% by wt. |
| 8 | | | 39.3 g/g | 7.4 g/g | 25.2% by wt. | 72.3 mN/m | 0.13% by wt. | 8.9% by wt. |
| 9* | Sorbitan monococoate | 100 ppm | 39.5 g/g | 7.1 g/g | 24.1% by wt. | 63.9 mN/m | 0.18% by wt. | 8.7% by wt. |
| 10* | Sorbitan monococoate | 166 ppm | 40.8 g/g | 7.2 g/g | 25.4% by wt. | 61.4 mN/m | 0.24% by wt. | 8.0% by wt. |

*Comparative
CRC Centrifuge retention capacity
AUL Absorption under a pressure of 21.0 g/cm²
Extr. Extractables
OFS Surface tension of the aqueous extract
Remos Residual monomers
<150 μm Undersize after roll mill

What is claimed:

1. A process for continuously producing water-absorbing polymer particles by polymerizing a monomer solution or suspension comprising
    a) at least one ethylenically unsaturated monomer which bears acid groups and optionally at least partly neutralized,
    b) at least one crosslinker,
    c) at least one initiator,
    d) optionally one or more ethylenically unsaturated monomers copolymerizable with the monomer a) and
    e) optionally one or more water-soluble polymers, comprising polymerizing, drying, grinding, classifying and at least partial recycling of undersize particles obtained in the classification, a polymer gel obtained by the polymerization being withdrawn from a polymerization reactor and mixed with the recycled undersize particles in an extruder, wherein a water content of a mixture obtained by mixing the polymer gel withdrawn from the polymerization reactor with the recycled undersize particles is from 40 to 70% by weight, essentially no surfactant is added in the mixing of the polymer gel withdrawn from the polymerization reactor with the recycled undersize particles and/or the surface tension of an aqueous extract of the water-absorbing polymer particles is at least 0.06 N/m, wherein the monomer a) is acrylic acid to an extend of at least 50 mol %.

2. The process according to claim 1, wherein the water content of the mixture obtained by mixing the polymer gel withdrawn from the polymerization reactor with the recycled undersize particles is from 50 to 65% by weight.

3. The process according to claim 1, wherein the polymer gel withdrawn from the polymerization reactor is mixed with the recycled undersize particles for from 1 to 180 minutes.

4. The process according to claim 1, which comprises at least one postcrosslinking.

5. The process according to claim 4, wherein the postcrosslinking is preceded and followed by classification.

6. The process according to claim 1, wherein polymerization is effected statically.

7. The process according to claim 1, wherein the polymer gel withdrawn from the polymerization reactor is mixed with the recycled undersize particles at a temperature of from 40 to 80° C.

8. The process according to claim 1, wherein a ratio of polymer gel to recycled undersize particles is from 5 to 50.

9. The process according to claim 1, wherein the water-absorbing polymer particles have a centrifuge retention capacity of at least 15 g/g.

* * * * *